US008895258B2

(12) United States Patent
Nam et al.

(10) Patent No.: US 8,895,258 B2
(45) Date of Patent: Nov. 25, 2014

(54) DEVICE FOR MEASURING PROTEINS USING BIOSENSOR

(71) Applicant: i-SENS, Seoul (KR)

(72) Inventors: Hakhyun Nam, Seoul (KR); Su-Moon Park, Gyeongsangbuk-do (KR); Jin-Young Park, Daejeon (KR); Joo Young Cho, Gyeonggi-do (KR)

(73) Assignee: i-SENS, Seoul (KR)

( * ) Notice: Subject to any disclaimer, the term of this patent is extended or adjusted under 35 U.S.C. 154(b) by 0 days.

(21) Appl. No.: 13/732,733

(22) Filed: Jan. 2, 2013

(65) Prior Publication Data
US 2013/0153443 A1 Jun. 20, 2013

Related U.S. Application Data

(62) Division of application No. 13/003,998, filed as application No. PCT/KR2009/002523 on May 13, 2009, now abandoned.

(30) Foreign Application Priority Data

Jul. 15, 2008 (KR) .................. 10-2008-0068740

(51) Int. Cl.
*G01N 33/543* (2006.01)
*G01N 33/53* (2006.01)
*G01N 27/02* (2006.01)

(52) U.S. Cl.
CPC ............ *G01N 27/02* (2013.01); *G01N 33/5438* (2013.01)
USPC .............................. 435/7.8; 435/7.1; 205/792

(58) Field of Classification Search
USPC .............. 436/512, 518–535; 435/4, 7.1–7.95; 204/403.01–403.15; 422/68.1, 82.01, 422/82.02; 600/345–361, 365
See application file for complete search history.

(56) References Cited

U.S. PATENT DOCUMENTS

| 5,242,842 | A | 9/1993 | Sundrehagen |
| 5,541,117 | A | 7/1996 | Karl et al. |
| 6,162,645 | A | 12/2000 | Lee et al. |
| 6,174,734 | B1 | 1/2001 | Ito et al. |
| 6,339,334 | B1 * | 1/2002 | Park et al. ............... 324/425 |

FOREIGN PATENT DOCUMENTS

| EP | 0455225 | 11/1991 |
| KR | 102007001429 A1 * | 2/2007 |
| KR | 1020070014292 | 2/2007 |

OTHER PUBLICATIONS

N. Kanayama, et al. "Interfacial recognition of sugars by boronic acid-carrying self-assembled monolayer", LANGMUIR, vol. 16, No. 2, 2000, p. 577-583.*
Park, et al., "Selective Electrochemical Sensing of glycated Hemoglobin (HbA1c) on Thiophene-3-Boronic Acid Self-Assembled Monolayer Covered Gold Electrodes", Analytical Chemistry, vol. 80, No. 21, Nov. 2008, p. 8035-8044.*

* cited by examiner

*Primary Examiner* — J. Christopher Ball
(74) *Attorney, Agent, or Firm* — Bachman & LaPointe, P.C.

(57) ABSTRACT

A sensor for measuring a concentration of a specific protein using a biosensor with a measurement speed improved from a conventional impedance measurement. The sensor is capable of efficiently and accurately measuring impedance generated by a selective binding to the protein by Fourier-transforming an electric current signal obtained by applying a potential signal of a delta function waveform. The device for measuring a protein using a biosensor is capable of measuring concentration of the protein with accuracy, measurement time is shortened and the concentration of protein can be accurately measured by removing the influence of dispersion.

13 Claims, 9 Drawing Sheets

DEVICE FOR MEASURING PROTEINS USING BIOSENSOR

CROSS-REFERENCE TO RELATED APPLICATIONS

This application is the divisional of U.S. patent application Ser. No. 13/003,998, filed Jan. 13, 2011 which is the U.S. national phase of International Application No. PCT/KR2009/002523, filed May 13, 2009, which claims priority of KR Application No. 10-2008-0068740, filed Jul. 15, 2008.

TECHNICAL FIELD

The present invention relates to a device for measuring proteins, and more particularly, to a device for measuring concentration of a specific protein contained in a sample using a biosensor, in which a receptor layer optionally binding to the specific protein is formed on an electrode and impedance generated due to the binding components is measured.

BACKGROUND ART

In recent, there have been increasing demands to measure blood glucose regularly to diagnose and prevent diabetes. Portable measuring instrument, to be specific, the strip-type biosensor is available for users to measure blood glucose easily and conveniently by simply grabbing the instrument in their hands.

U.S. Pat. No. 5,541,117 discloses preparing a pad with glycosylated haemoglobin assay-specific antibody fixed thereon, transferring the sample onto the fixed pad, and performing computation based on the intensity of reflected light. However, it has shortcomings in that expensive antibody is required, and sensors with consistent quality can hardly be achieved due to the inequalities of porous pad.

U.S. Pat. No. 5,242,842 discloses mixing boronic acid derivatives and glycosylated protein, and measuring blood glucose by spectroscopic method after precipitation or lysis. However, it has difficulties as it requires washing process of boronic acid derivatives, which are lysed with glycosylated protein, and a precise amount of sample should always be maintained to ensure the right results.

Also, U.S. Pat. No. 6,162,645, EP0455225B1 and U.S. Pat. No. 6,174,734 disclose a method of separating protein from sample using solid phase to which immune body is fixed, and determining a relative amount of glycosylated protein using marker compound. However, these conventional electrochemical determining methods of glycosylated protein generally involve collecting glycosylated protein and glycosylated protein-markers competitively on the surface of electrode, and injecting substrate, which stimulates electrochemical reaction with marker, to determine the size of the signal, and is thus has complicated measurement of the concentration of glycosylated protein and can hardly be reproducible.

DISCLOSURE

Technical Problem

To solve the above problems, the present invention provides a device for measuring protein using biosensor, in which delta function waveform is applied, and impedance of the current signals is computed by Fourier transform to efficiently and accurately measure the concentration of a specific protein in a sample.

Technical Solution

In order to achieve the above-mentioned object, a device for measuring a protein using a biosensor is provided, which may include the biosensor comprising a sample inlet through which a sample is drawn in, a working electrode on which a receptor layer is coated for selective binding to the specific protein in the drawn sample, and a measuring unit including a reference electrode to form a potential difference with the working electrode, a function generator which applies a potential signal in the form of delta function to the working electrode and the reference electrode, and a data processing unit which measures impedance of the working electrode by Fourier-transforming an electric current obtained in response to the delta function waveform.

The measuring unit additionally includes an auxiliary electrode to measure impedance of the working electrode, and the delta function waveform is applied between the working electrode and the auxiliary electrode.

The protein is a glycated hemoglobin protein formed as hemoglobin is transformed by combining with glucose.

The receptor layer is formed as a self-assembled monolayer (SAM) which have boronic acid derivative as end group.

The concentration of the specific protein is measured by measuring impedance generated on the working electrode by selective binding to the receptor layer.

The function generator integrates the delta function waveform and applies a step potential signal.

The biosensor additionally includes an air outlet for the sample to move through the sample inlet to the measuring unit by capillary phenomenon.

The device additionally includes an electrochemical biosensor which is connected to the sample inlet through a micro channel, and which measures an amount of hemoglobin by the oxidation-reduction reaction of hemoglobin contained in the sample.

The device additionally includes a plunger into which capillary blood collecting tube is easily inserted and engaged to measure the glycated hemoglobin and the hemoglobin simultaneously; a body which accommodates a buffer solution containing a hemolytic substance and a oxidation-reduction pair; and a pretreatment sample feeding unit which includes an outlet in which a filter on an end of the body.

The working electrode is made from gold or white gold.

The receptor layer is formed as a self-assembled monolayer having boronic acid derivative as an end group, and the boronic acid derivative is partially transformed into a thiol group to easily combine with a gold electrode.

The data processing unit measures impedance which occurs when electron transfer of an oxidation-reduction pair is inhibited by a protein selectively the receptor layer on the working electrode.

The oxidation-reduction pair is selected from a group consisting of ferrocene, ferrocene derivatives, quinones, quinines derivatives, organic conducting salt, or viologen, hexaammineruthenium (III) chloride, dimethylferrocene (DMF), ferricinium, ferrocene monocarboxylic acid (FCOOH), 7,7,8,8-tetracyanoquino-dimethane (TCNQ), tetrathia fulvalene (TTF), nickelocene (Nc), N-methyl acidinium (NMA+), tetrathiatetracene (TTT), N-methylphenazinium (NMP+), hydroquinone, 3-dimethylaminobenzoic acid (MBTH-DMAB), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone, and benzidine.

Advantageous Effects

With the device according to the present invention, measurement time is shortened and the concentration of proteins may be accurately measured.

Also, due to the shortened time, S/N ratio is drastically increased by multiple measurements.

In measuring the concentration of glycated protein, the concentrations of hemoglobin and glycated hemoglobin may be measured without separating process of hemoglobin and glycated hemoglobin to measure the ratio of them.

The amount of glycated protein may be rapidly and accurately measured improving accuracy and reliability, and the device of the present invention may be available for disposable sensor.

DESCRIPTION OF MAIN ELEMENTS OF THE DRAWINGS function generator: 110 potentiostat: 120
measurement device: 130 data processing device: 140
[Best Mode]

A device for measuring protein using biosensor according to the present invention will be explained in greater detail below.

Figure 1:
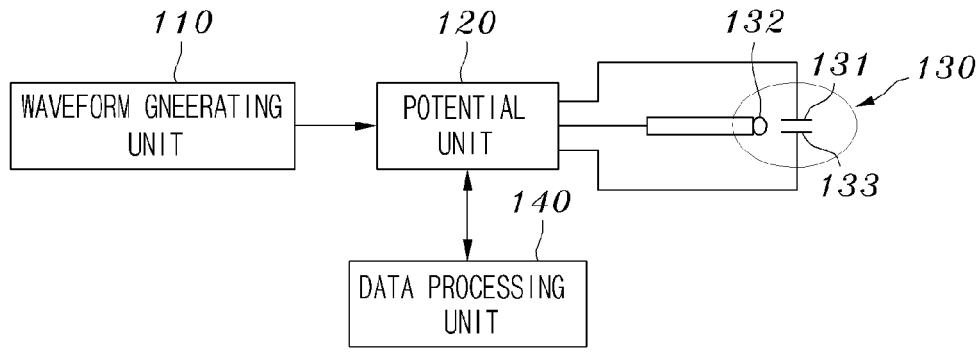
FIG. 1 illustrates the brief description of a device for measuring protein using biosensor according to the present invention.

FIG. 1 is a schematic view of a device for measuring protein using biosensor according to an embodiment. Referring to FIG. 1, the device for measuring the concentration of glycated protein according to the embodiment may include a function generator (110), a potentiostat (120), a biosensor (130), and a data processing unit (140) to measure concentration of the glycated protein efficiently and accurately based on impedance measured using the Fourier transformation.

Figure 2:
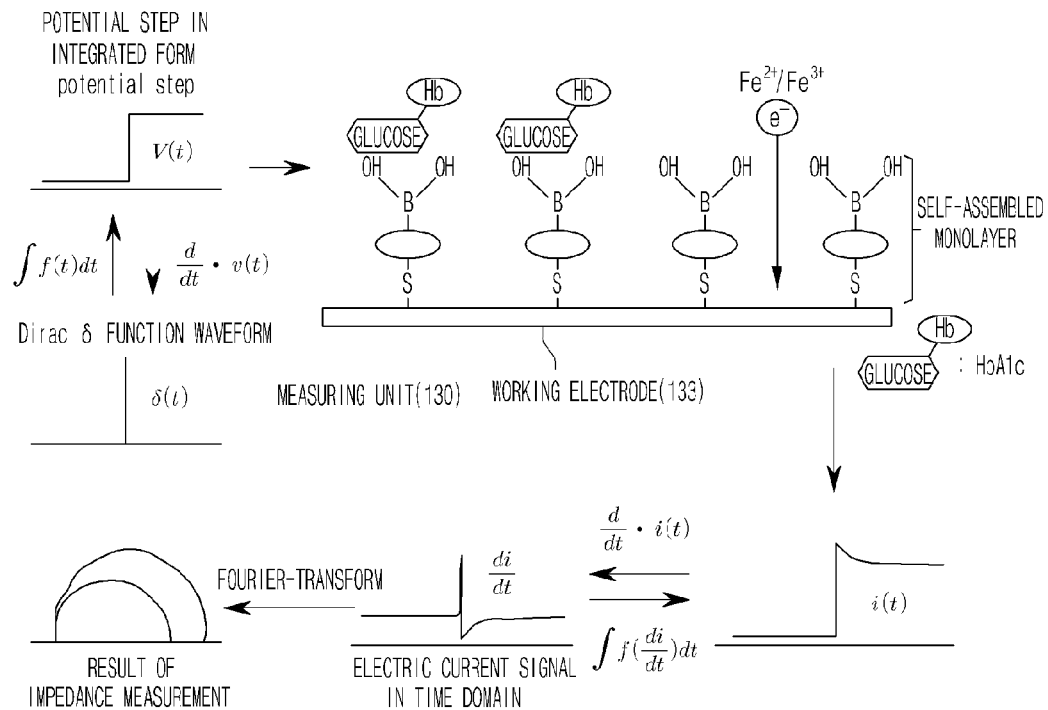
FIG. 2 illustrates the principles of fourier transform according to the present invention.

The principle of measuring glycated protein according to the embodiment is schematically illustrated in FIG. 2. As the concentration of glycated protein in blood increases, binding to the molecules of a self-assembled monolayer (SAM) coated on the surface of electrode increases, and impedance, which inhibits electron transfer of materials from oxidation-reduction such as $Fe(CN)_6^{3-}/Fe(CN)_6^{4-}$ or $Ru(NH_3)^{3+}/Ru(NH_3)^{2+}$ on the surface of electron, increases. Therefore, the impedance is measured by performing fourier transform to measure the concentration of glycated protein in the sample.

The materials of electron transfer oxidation-reduction may be mixing electrons such as ferrocene, ferrocene derivative, quinones, quinones derivatives, organic conducting salt, or viologen, hexaammineruthenium (III) chloride, potassium ferricyanide, potassium ferrocyanide, dimethylferrocene (DMF), ferricinium, ferocene monocarboxylic acid (FCOOH)), 7,7,8,8-tetracyanoquino-dimethane (TCNQ), tetrathia fulvalene (TTF), nickelocene (Nc), N-methyl acidinium (NMA+), tetrathiatetracene (TTT), N-methylphenazinium (NMP+), hydroquinone, 3-dimethylaminobenzoic acid (MBTHDMAB), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5-tetramethyl benzidine (TMB), 2,2-azino-di-[3-ethyl-benzthiazoline sulfonate], o-dianisidine, o-toluidine, 2,4-dichlorophenol, 4-amino phenazone, benzidine, or prussian blue.

Unlike the conventional frequency response analyzer (FRA) which measures impedance by perturbing each frequency with the alternating current (AC) and using an AC value generated as a result of applying the perturbation to chemical reaction system, the device for measuring protein according to the present invention applies integral delta wave form of the waveform consisting of all the AC frequencies with the same amplitude and phase to drastically shorten the measuring time. That is, the function generator applies pulse potential step, which is the integral form of the delta function waveform, measures the electric current as generated, and performs Fourier transformation to measure impedance. As illustrated in FIG. 2, the integral of the delta waveform is same as the pulse potential step and can be used with a conventional electric device (J.-S. Yoo and S.-M. Park, *An Electrochemical Impedance Measurement Technique Employing Fourier Transform Anal. Chem.*, 72, 9, 2035-2041, 2000). It is desirable that potential-electric functions have a linear relationship to be able to apply integral pulse potential step to electrochemical system. Although embodiments according to the present invention described herein apply 5-15 mV of relatively low delta pulse potential step, but the desirable range of potential step is not limited to these specific examples only.

The function generator (110) is like an electric device which generates delta pulse potential step. The potentiostat (120) receives delta pulse potential step generated by the random function generator (110) and applies DC electric potentials to a chemical reactive system, and is used for more efficient and stable application of the electric potential.

The measurement unit (130) of the biosensor includes an auxiliary electrode (131) and a reference electrode, and boronic acid derivative, having the selective binding ability to glycated protein, coated in the form of a self-assembled monolayer (SAM) on a working electrode (133). The auxiliary electrode is desirably made from a conductive material which does not chemically react with the measuring sample, and the reference electrode desirably includes silver/silver chloride electrode or similar reference electrode. The working electrode desirably includes gold, silver or copper substrate, or any of the material advantageous for SAM formation. The SAM molecules, formed on the surface of working electrode (133) of the measuring unit (130) due to the existence of glycated protein in blood, bind to the glycated protein. The efficiency of oxidation-reduction of the electroactive species in the solution, such as $Fe(CN)_6^{3-}/Fe(CN)_6^{4-}$, depends on the number of SAM-glycated protein formed on the surface of electrode by such binding, and the amount of the electricity is measured by the potentiostat (120) by the electrochemical method. The measured electric signal by the potentiostat (120) is transferred to the data processing unit (140), and impedance is measured by performing Fourier transformation with respect to the electric current signal measured by chronoamperometry in the process as illustrated in FIG. 2.

In one embodiment, the impedance measurement involves applying delta pulse potential step of differential function, measuring and differentiating the corresponding signal, and performing Fourier transformation to obtain the result. As the measuring time is within 2 ms, the concentration of the sample is accurately measured without dispersion, and S/N ratio is drastically improved due to accumulation of multiple signals for a predetermined time period.

Figure 3:
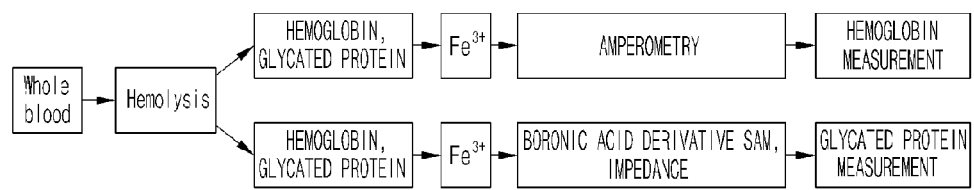
FIG. 3 illustrates a brief description of measuring method according to the present invention.

The amount of glycated hemoglobin of glycated protein is often represented as the relative amount of glycated hemoglobin to a total amount of hemoglobin in blood. Since it is necessary to measure the total amount of hemoglobin to obtain the amount of glycated hemoglobin, conventionally, hemoglobin and glycated hemoglobin have to be separated from each other before such measurement. However, as illustrated in FIG. 3, the sensor for measuring glycated hemoglobin according to the present invention uses $Fe^{3+}$ as the reaction index material of hemoglobin and glycated hemoglobin, and thus requires no separation process for the measurement.

Figure 4:
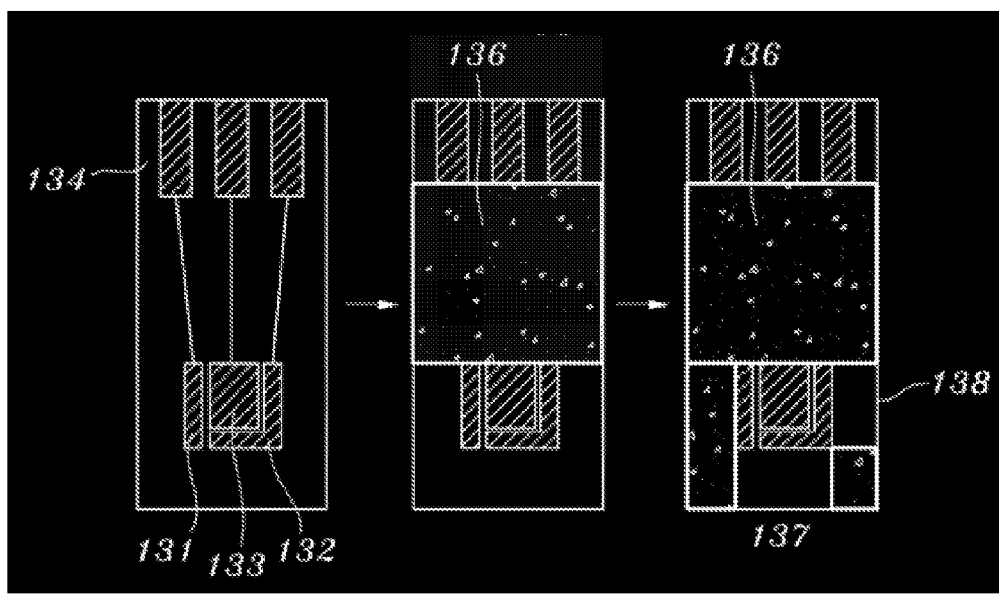
FIG. 4 illustrates a front view of measurement sensor according to the present invention.

Hemoglobin is measured by the electrochemically measuring electric current from reversible oxidation-reduction reaction between $Fe^{2+}$ in HEME group and $Fe^{3+}$ in buffer solution. Compared to the conventional method of measuring hemoglobin, the measurement method according to the present invention requires no separation of hemoglobin and glycated protein, and as illustrated in FIG. 4, provides sensors attached to the respective measuring materials. The measuring sensors each consists of a gold working electrode (133), an auxiliary electrode (132), a silver/silver chloride reference electrode (131), and an electric connecting line 134 which connects the respective electrodes to a measurement device. An insulation layer of insulation material is formed except on the area except for the portions where the three electrodes are formed. The capillary phenomenon is utilized to measure a small amount of blood sample within a short time, a double-sided tape (136) is attached to form a micro channel. The measuring sensor also includes a solution inlet (137) through which measuring solution is fed, and an air outlet (138) to ensure efficient feeding of the measuring solution. The sensor for measuring glycated protein forms, SAM structure using the above-mentioned boronic acid derivative on the surface of gold working electrode (133), while the sensor for measuring hemoglobin does not treat the surface of gold working electrode (133).

Figure 5:
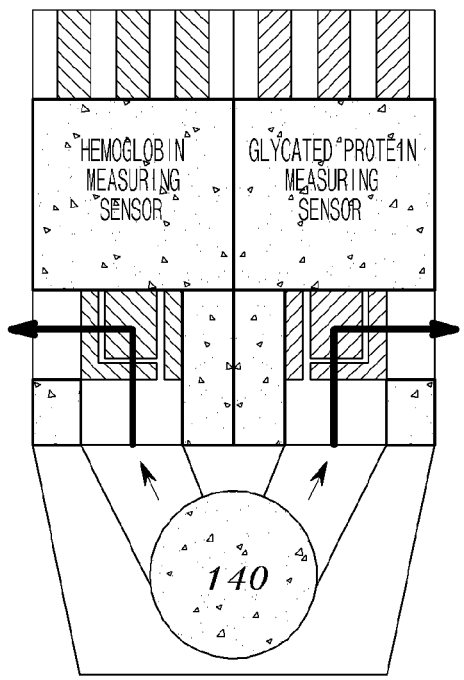
FIG. 5 illustrates a front view of measurement sensor cartridge according to the present invention.

FIG. 5 illustrates the manner of feeding measuring solution including hemolysis reagent, buffer solution, and Fe3+, added with a predetermined amount of blood into each electrode. To measure hemoglobin and glycated protein, two electrodes according to FIG. 4 are inserted into the measuring device, and after undergoing hemolytic process, the solution is fed into the solution inlet 140 (140), so that a small amount of solution is moved into each electrode through channel by capillary phenomenon.

Figure 6:
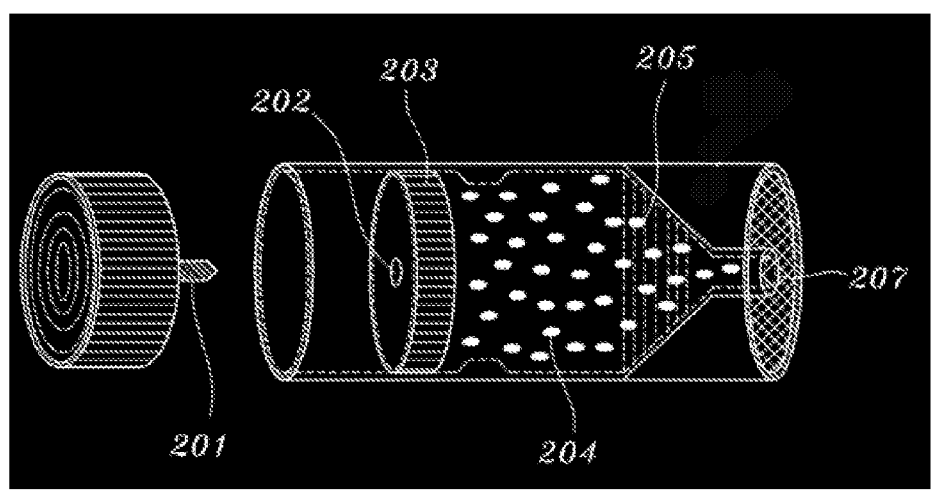
FIG. 6 illustrates a mimetic diagram of a device of blood blend/injection in a syringe form according to the present invention.

FIG. 6 illustrates a method of changing whole blood by hemolysis into measuring solution for the measurement of glycated protein and hemoglobin. A predetermined amount of blood is taken by capillary blood collection with transfusion needle (201), injected into receiver blood injection port (202) with easily tearable layer, and according to the piston movement of a syringe, the blood is pushed into plunger (203) i.e., to the solution (204) including a mixture of hemolysis reagent, buffer solution, and $Fe^{3+}$. Any solid substance in the mixture of the solution (204) and blood is removed by filter (205). The mixed measuring solution is injected and held in the solution receiver (137) through a solution injecting port (207). Lid (207) is employed to prevent contamination before mixing and sample injecting.

The present inventive technical concept will be explained in greater detail below based on the exemplary embodiments, but the effects of the present invention are not to be limited to the specified examples only.

Embodiment 1

Measurement of Glycated Protein Based on Impedance Using Fourier Transform

The experiment is based on the method and principle explained above, with the following conditions of the experiment. The buffer solution used blank solution of pH 7.4, 10 mM PBS and 2.5 mM $Fe^{3+}$, hemolysis blood sample was used, and glycated hemobligin was used in a concentration of 4.5%, 5.2%, 7.0%, 9.2% and 11.6%. The SAM was formed on the gold working electrode (133) using 10 mM thiophene boronic acid.

Figure 7:
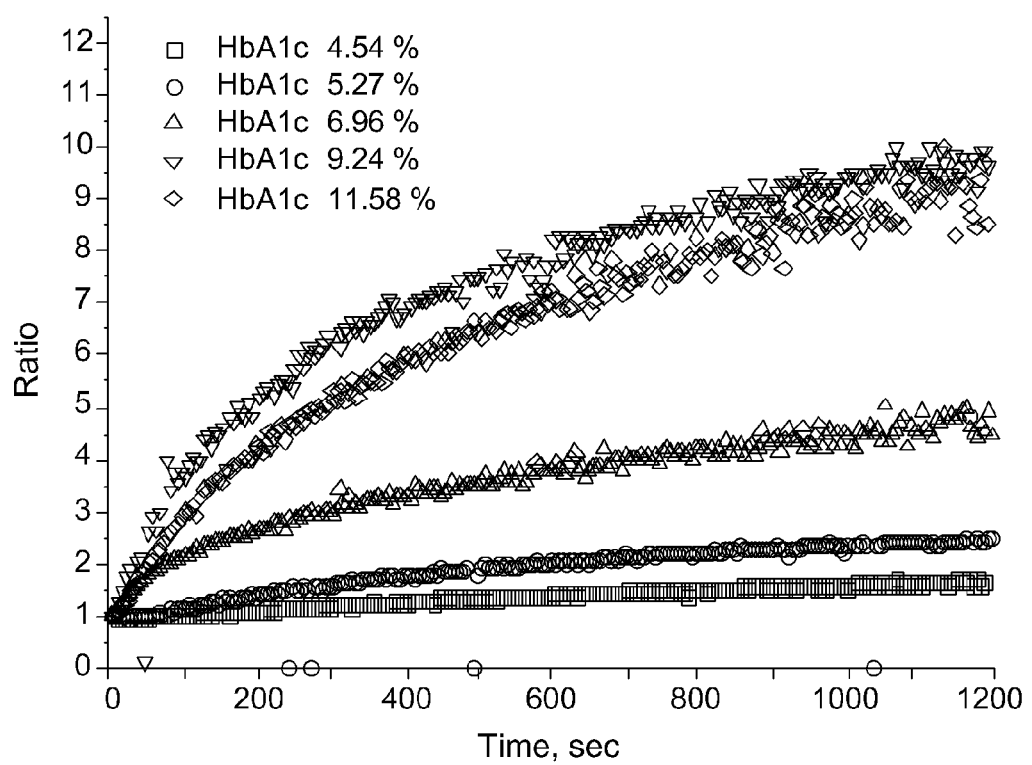
FIG. 7 illustrates sensitivity dispersion of glycated protein by performing fourier transform according to the present invention.

The graphical representation of sensitivity of FIG. 7 indicates the result of measurement in which randomized controlled trial (Rct) was measured according to each concentration and represented in the form of ratio of the blank solution with respect to charge transfer resistance. FIG. 7 represents the measurement of impedance using frequency response analyzer (FRA). The conventional method requires long measurement time and long data processing time to measure the average signal to improve signal-to-noise ratio efficiently. However, in the measurement method according to the present invention, various frequencies from a wide range are applied at once as the delta function waveforms, to thus greatly shorten the measurement time, and it is possible to monitor electric-chemical reactions such as impedance measurement within a short time of 50 ms or so.

Figure 8:
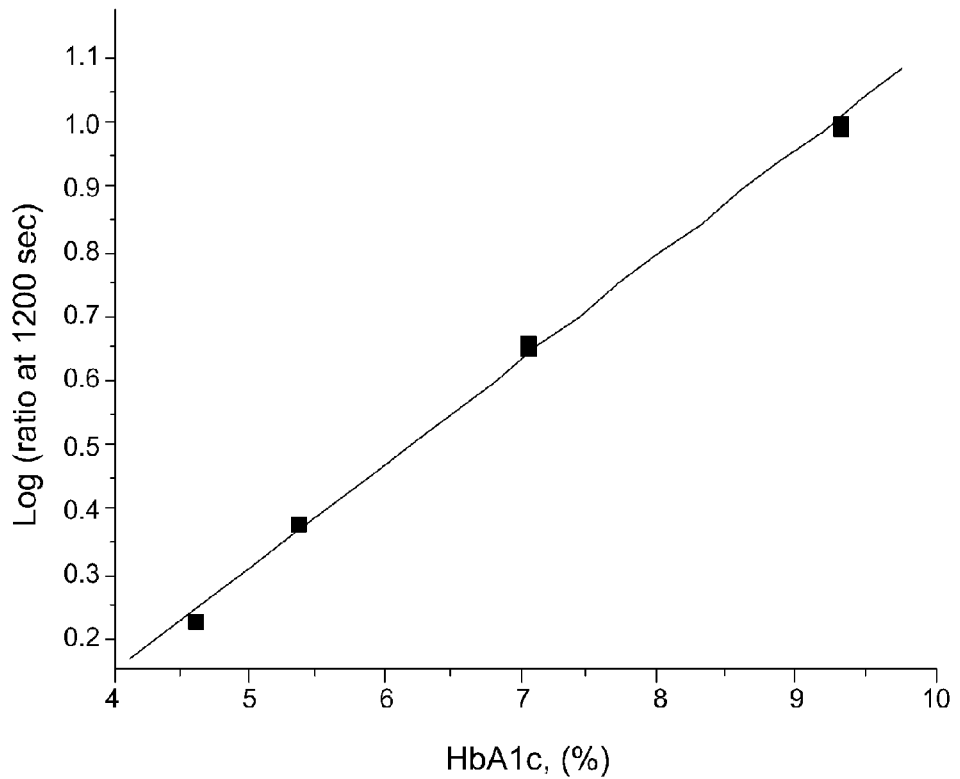
FIG. 8 illustrates callibration lines of glycated protein by performing fourier transform according to the present invention.

FIG. 8 is calibration line representing the log value of the average of charge transfer resistance. The linearity of the calibration line indicates that the impedance measurement method according to the present invention is adaptable as the biosensor.

MODE FOR INVENTION

Embodiment 2

Measurement of Glycated Protein Through Frequency Sensitivity Analysis Impedance The present invention provides a sensor for measuring glycated protein using Fourier transformation. The acceptability of the impedance measurement for use as a glycated protein sensor was confirmed using the conventional frequency response analyzer and measuring impedances according to the respective concentrations of the glycated proteins.

Figure 9:
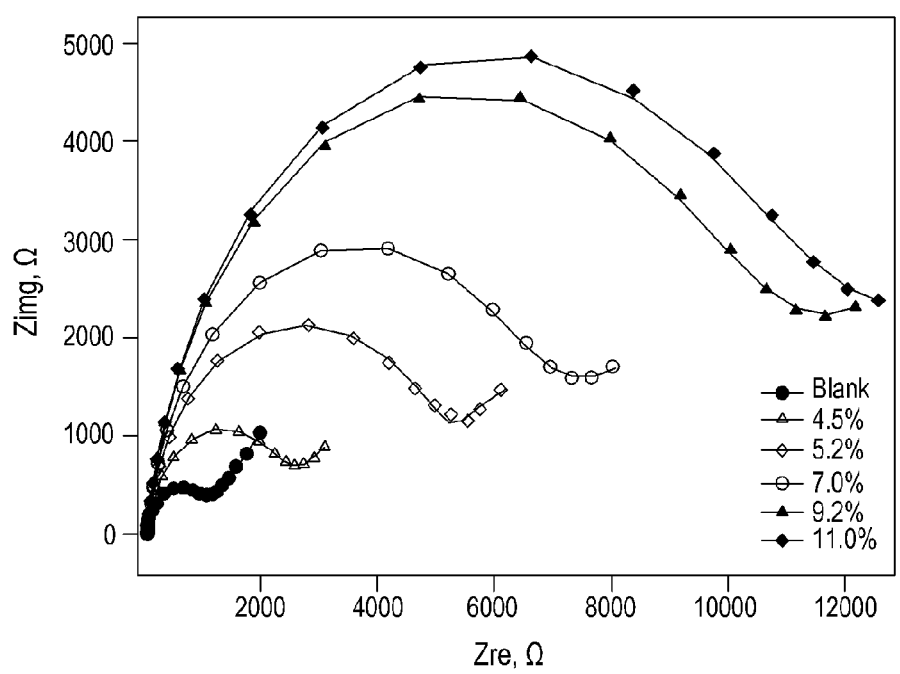
FIG. 9 illustrates sensitivity curves of glycated protein by performing frequency response analyzer (FRA) according to the present invention.
Figure 10:
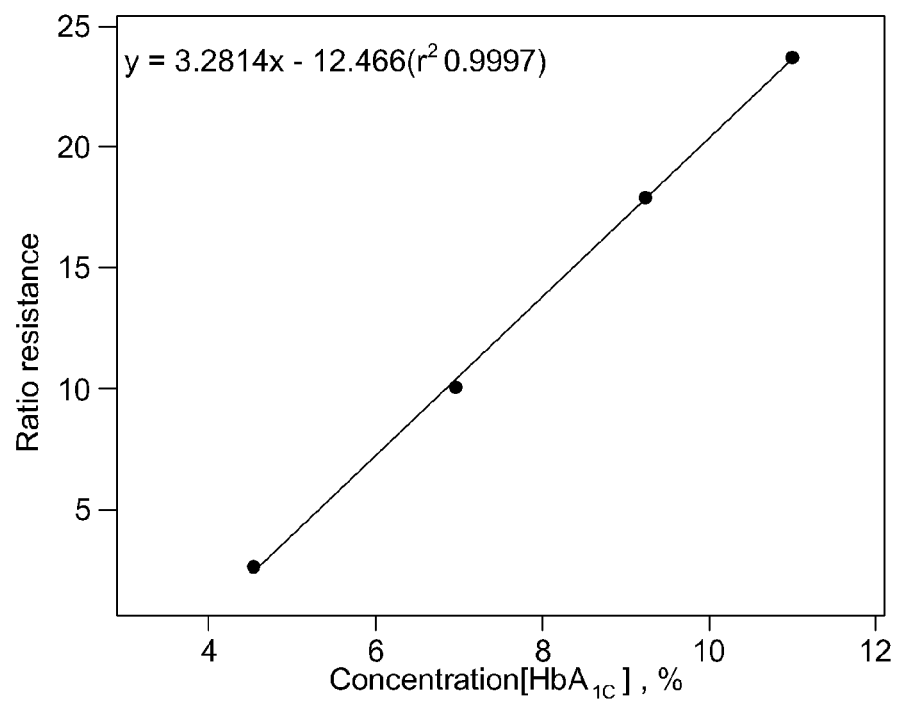
FIG. 10 illustrates callibration line of glycated protein by performing frequency sensitivity analyzer according to the present invention.

Embodiment 2 applied the same method explained above in Embodiment 1, and the graphical representation of sensitivity and the calibration line of FIGS. 9 and 10 respectively represent the result of measurement.

Referring to FIGS. 9 and 10, the linear increment of impedance in accordance with the increase of concentration of glycated protein confirms the suitability of a device according to the present invention as a biosensor using impedance and also confirms that glycated protein is effectively detected by the impedance method using Fourier transformation.

Embodiment 3

Measurement of Glycated Hemoglobin Using Fourier-Transformed Impedance

Figure 11:
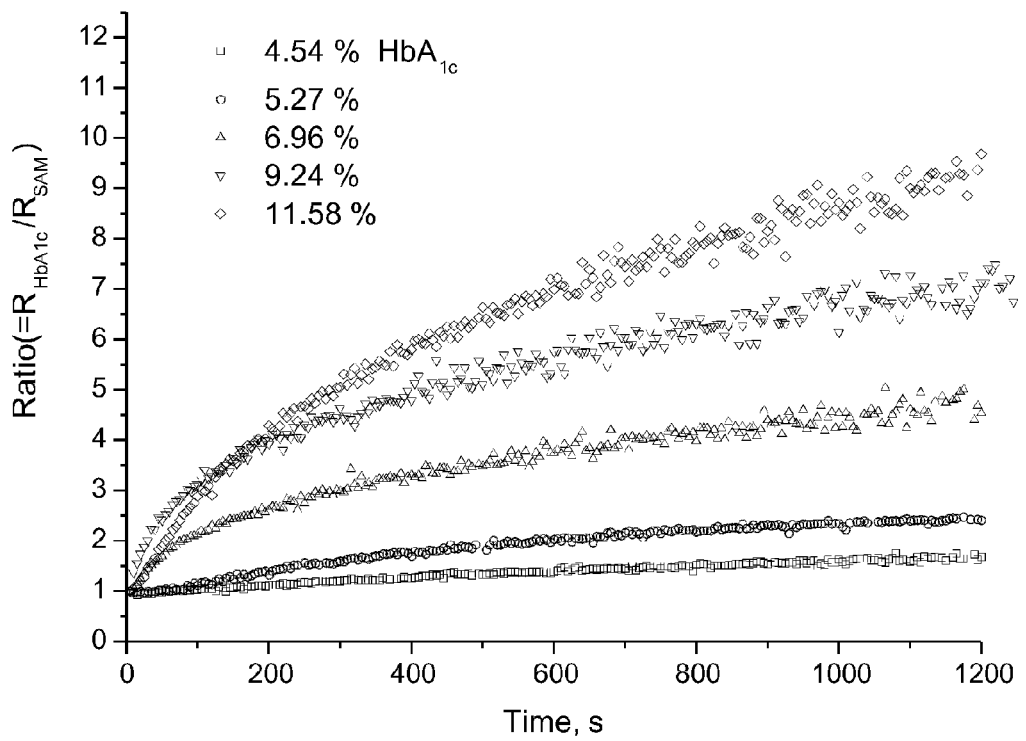
FIGS. 11 and 12 illustrate a callibration line of electron transfer resistivity: 4.54, 5.27, 6.96, 9.24 and 11.58% of glycated protein including sample according to the changes of impedance by performing fourier transform and hemoglobin.
Figure 12:
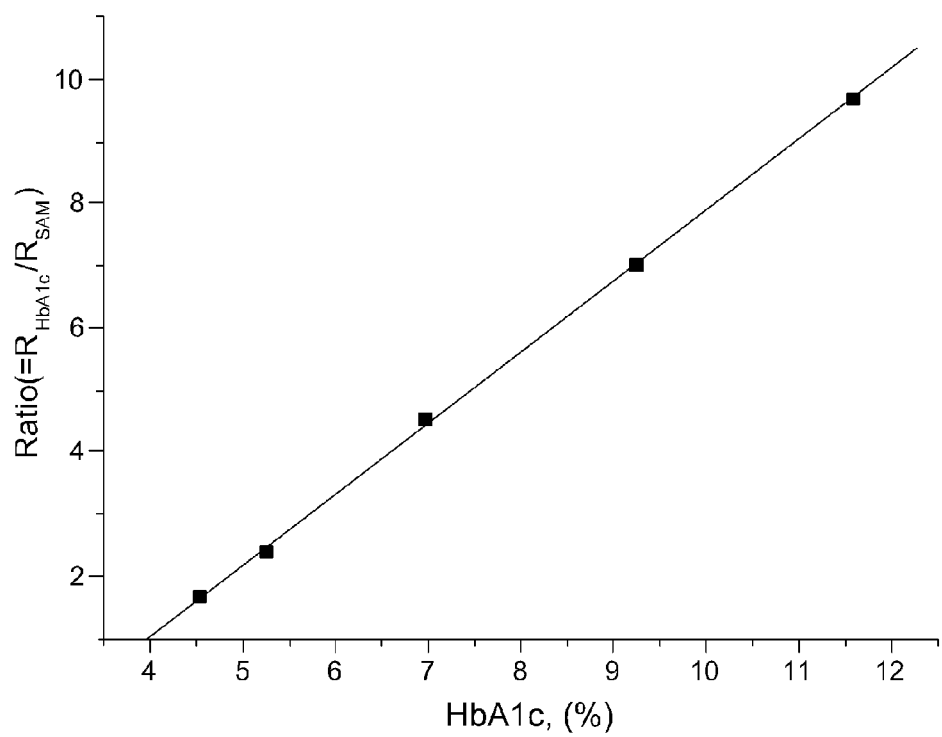

The method using Fourier-transformed impedance was applied to the electrode of Embodiment 1 by using a potentiostat which has the potential increasing time shorter than 50 ms. Impedance data was collected for the first 2.5 seconds by using 10 mv potential step corresponding to 0.4 Hz. From the data obtained from chronoamperometry, impedance data was computed within a range of 0.4-10 kHz, and cyclic voltammetry was conducted at 400 mV/s scan speed for 2.5 seconds. Stock solution in various concentrations was prepared from 4 mL pH 8.5 buffer solution, and 40 µL was taken from each stock solution and injected into solution containing electrode and oxidation-reduction pair to measure the charge transfer resistance. As for standard substance, JCCLS CRM004a (Japanese Committee for Clinical laboratory Standards) containing 4-13% of glycated hemoglobin with respect to the total amount of hemoglobin (140±10 g/L) was used. Impedance was obtained by differentiating the step potential difference, and converting the chronoamperometry result obtained from the step potential difference from the time domain to the frequency domain of 0.4-10 kHz. The data was measured for 20 minutes. The result is disclosed in FIG. 11, and it shows that regardless of the amount of hemoglobin in the sample, the result is in proportion to the amount of glycated hemoglobin.

Industrial Applicability

According to the present invention, concentration of a specific protein in the sample is measured accurately and rapidly, and as the measurement time is short, S/N ratio is greatly improved with multi measurement. Furthermore, when the concentration of glycated protein is measured, concentration of hemoglobin and glycated hemoglobin can be measured and thus the ratio of the two materials can be obtained, without requiring a process of separating hemoglobin and glycated hemoglobin.

Furthermore, since it is possible to quantitatively measure the amount of glycated protein, measurement with improved accuracy and reliability is provided. Furthermore, the invention also has the industrial availability since it is suitable for disposable sensor.

The invention claimed is:

1. A method of measuring a concentration of a specific protein using a biosensor comprising:
feeding a sample comprising the specific protein into a biosensor;
wherein the biosensor comprises a sample inlet through which the sample is drawn in, a working electrode on which a receptor layer is coated for selective binding to the specific protein in the drawn sample, and a measuring unit comprising a reference electrode to form a potential difference with the working electrode,
applying a potential signal in a form of delta function waveform to the working electrode and the reference electrode; and
measuring an impedance of the working electrode by Fourier-transforming an electric current obtained in response to the delta function waveform,
wherein the specific protein is a glycated protein, and the receptor layer is formed as a self-assembled monolayer (SAM) which have boronic acid derivative as an end group.

2. The method of claim 1,
wherin
the sample is a measuring solution comprising a hemolysis reagent, a buffer solution, an ion of $Fe^{3+}$ and a sample of blood.

3. The method of claim 2, further comprising measuring a concentration of a hemoglobin contained in the sample by an oxidation-reduction reaction of the hemoglobin using other electrochemical biosensor which is connected to the sample inlet through a micro channel.

4. The method of claim 1, wherein the measuring unit further comprises an auxiliary electrode to measure impedance of the working electrode, and the potential signal is applied between the working electrode and the auxiliary electrode.

5. The method of claim 1, wherein the concentration of the specific protein is measured by measuring impedance generated on the working electrode by selective binding to the receptor layer.

6. The method of claim 1, wherein the potential signal is applied as a step potential signal by integrating the delta function waveform.

7. The method of claim 1, wherein the biosensor further comprises an air outlet for the sample to move through the sample inlet to the measuring unit by capillary phenomenon.

8. The method of claim 1, wherein the working electrode is made from gold or white gold.

9. The method of claim 8, wherein the receptor layer is formed as a self-assembled monolayer having boronic acid derivative as an end group, and the boronic acid derivative is partially transformed into a thiol group to easily combine with a gold electrode.

10. The method of claim 1, wherein the impedance occurs when electron transfer of an oxidation-reduction pair is inhibited by the specific protein selectively binding to the receptor layer on the working electrode.

11. The method of claim 10, wherein the oxidation-reduction pair is selected from a group consisting of ferrocene, ferrocene derivatives, quinones, quinines derivatives, organic conducting salt, or viologen, hexaammineruthenium (III) chloride, dimethylferrocene (DMF), ferricinium, ferocene monocarboxylic acid (FCOOH), 7,7,8,8-tetracyanoquinodimethane (TCNQ), tetrathia fulvalene (TTF), nickelocene (Nc), N-methyl acidinium (NMA+), tetrathiatetracene (TTT), N-methylphenazinium (NMP+), hydroquinone, 3-dimethylaminobenzoic acid (MBTHDMAB), 3-methyl-2-benzothiozolinone hydrazone, 2-methoxy-4-allylphenol, 4-aminoantipyrin (AAP), dimethylaniline, 4-aminoantipyrene, 4-methoxynaphthol, 3,3',5,5'-tetramethyl benzidine (TMB), 2,2-azino-di-[3-ethyl-benzthiazoline sulfonate], o-dianisidine, o-toluidine, 2,4-dichlorophenol, 4-amino phenazone, benzidine and prussian blue.

12. A method of measuring a concentration of a specific protein using a biosensor comprising:
    feeding a sample comprising the specific protein into a biosensor;
    wherein the biosensor comprises a sample inlet through which the sample is drawn in, a working electrode on which a receptor layer is coated for selective binding to the specific protein in the drawn sample, and a measuring unit comprising a reference electrode to form a potential difference with the working electrode,
    applying a potential signal in a form of delta function waveform to the working electrode and the reference electrode; and
    measuring an impedance of the working electrode by Fourier-transforming an electric current obtained in response to the delta function waveform,
    wherein the specific protein is a glycated protein, and, the receptor layer is formed as a self-assembled monolayer (SAM) which have boronic acid derivative as an end group, and the boronic acid derivative is partially transformed into a thiol group to easily combine with the working electrode.

13. A method of measuring a concentration of a specific protein using a biosensor consisting essentially of:
    feeding a sample comprising the specific protein into a biosensor;
    wherein the biosensor comprises a sample inlet through which the sample is drawn in, a working electrode on which a receptor layer is coated for selective binding to the specific protein in the drawn sample, and a measuring unit comprising a reference electrode to form a potential difference with the working electrode,
    applying a potential signal in a form of delta function waveform to the working electrode and the reference electrode; and
    measuring an impedance of the working electrode by Fourier-transforming an electric current obtained in response to the delta function waveform,
    wherein the specific protein is a glycated protein, and the receptor layer is formed as a self-assembled monolayer (SAM) which have boronic acid derivative as an end group.

* * * * *